(12) United States Patent
Roselauf et al.

(10) Patent No.: US 9,592,144 B2
(45) Date of Patent: Mar. 14, 2017

(54) BYPASS DEVICE, SUPPORT FRAME FOR BYPASS DEVICE, AND METHOD

(71) Applicant: TERUMO KABUSHIKI KAISHA, Shibuya-ku (JP)

(72) Inventors: Brian Roselauf, Rancho Santa Margarita, CA (US); Jonathan Phan, Garden Grove, CA (US)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 319 days.

(21) Appl. No.: 14/156,030

(22) Filed: Jan. 15, 2014

(65) Prior Publication Data

US 2015/0196414 A1   Jul. 16, 2015

(51) Int. Cl.
*A61M 5/00* (2006.01)
*A61F 5/00* (2006.01)
*A61F 2/07* (2013.01)
*A61F 2/04* (2013.01)

(52) U.S. Cl.
CPC .......... *A61F 5/0076* (2013.01); *A61F 5/0079* (2013.01); *A61F 2/04* (2013.01); *A61F 2/07* (2013.01)

(58) Field of Classification Search
CPC ........ A61F 5/0076; A61F 5/0079; A61F 2/04; A61F 2/07; A61F 2/86; A61F 2/88; A61F 2002/045; A61F 2002/044; A61F 2002/9511; A61F 2220/016; A61F 2220/0008
See application file for complete search history.

(56) References Cited

U.S. PATENT DOCUMENTS

| | | | |
|---|---|---|---|
| 7,476,256 B2 | 1/2009 | Meade et al. | |
| 8,414,635 B2 | 4/2013 | Hyodoh et al. | |
| 2009/0177272 A1* | 7/2009 | Abbate | A61K 9/70 623/1.42 |
| 2010/0256775 A1* | 10/2010 | Belhe | A61F 5/0076 623/23.65 |
| 2010/0305590 A1 | 12/2010 | Holmes et al. | |

FOREIGN PATENT DOCUMENTS

JP   2004-167239 A   6/2004

* cited by examiner

*Primary Examiner* — Philip R Wiest
*Assistant Examiner* — Ariana Zimbouski
(74) *Attorney, Agent, or Firm* — Buchanan Ingersoll & Rooney PC

(57) ABSTRACT

A liner support frame is configured to be positioned in a gastrointestinal tract of a human and to support a liner which inhibits nutrient absorption and anchor the liner in place in the gastrointestinal tract, the liner support frame includes a plurality of frame members connected to one another so that the liner support frame possesses a plurality of openings. The liner support frame includes a plurality of frame portions arranged axially and possessing different tapers.

7 Claims, 6 Drawing Sheets

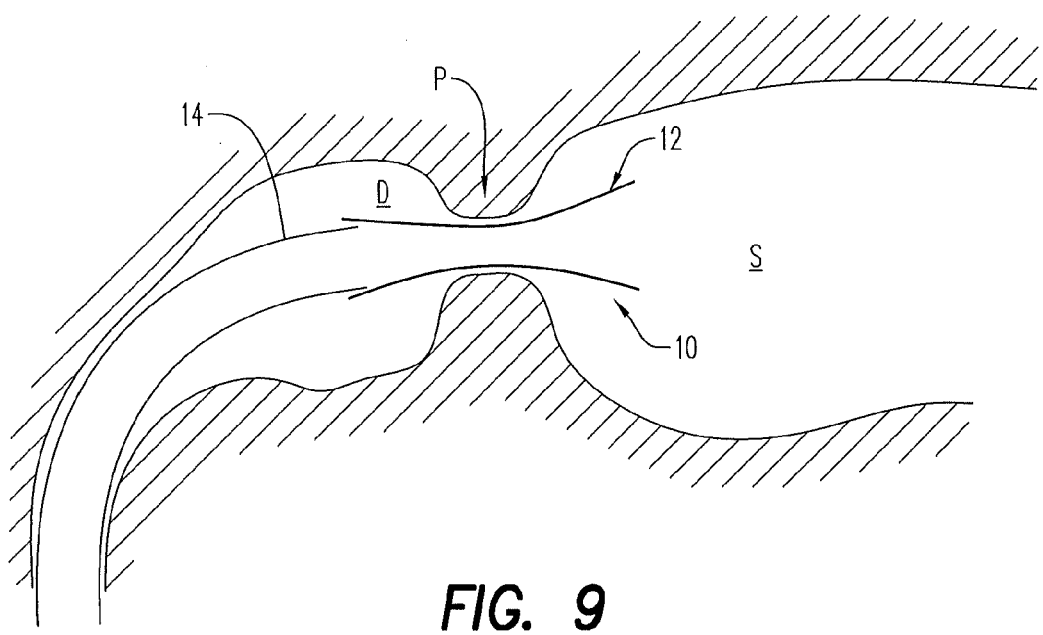
FIG. 9
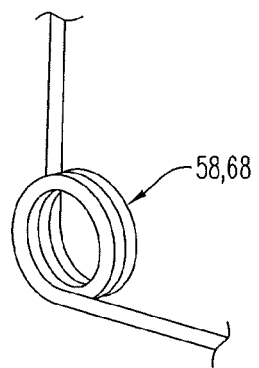
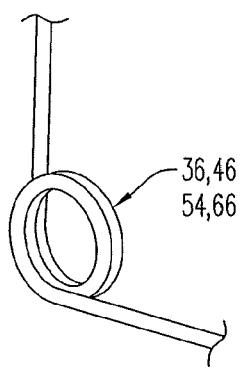
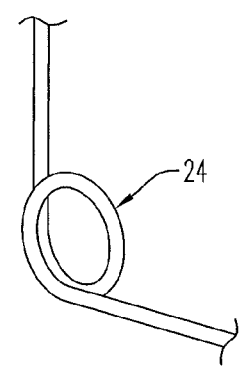
FIG. 10A    FIG. 10B    FIG. 10C

BYPASS DEVICE, SUPPORT FRAME FOR BYPASS DEVICE, AND METHOD

TECHNICAL FIELD

The present invention generally pertains to a bypass device configured to be positioned in the gastrointestinal tract of a patient (human being). The invention also relates to a support frame to be used in a bypass device and a method.

BACKGROUND DISCUSSION

Many patients suffer from poor glycemic control. The reasons are quite varied, involving, for example, delayed treatment, failure to improve lifestyle, discontinued treatment, and the natural limits of the treatment itself. If the patient's pathology has progressed to the point of requiring insulin therapy, there are few appropriate measures available to stop the insulin therapy. It is thus desirable to take action that would lessen the possibility of becoming dependent on insulin therapy.

Bypass surgery has been used to address obesity, and this has resulted in a relatively high rate of treatment for type2 diabetes. Nevertheless, bypass surgery has not been widely adopted as the standard of care for diabetes because it is highly invasive to the patient.

There are known sleeve-type devices configured to be positioned in the stomach or upper intestines. These devices typically include a sleeve fixed to an anchor structure. The anchor structure serves as an anchor of sorts for anchoring the sleeve in position so that the sleeve lines the upper intestines. The sleeve operates to inhibit the absorption of food nutrients across the gastrointestinal tract. These known devices suffer from a variety of shortcomings. That is, they cause nausea, upper abdominal pain, inflammation at the implant site and vomiting. Other complications that have been experienced with the known devices include lumen obstruction and migration of the device. The occurrence of some of these difficulties may necessitate early removal of the device, rather than intended removal through the course of therapeutic treatment.

The anatomy of the gastrointestinal tract presents particular challenges when considering an appropriate configuration for the structure for anchoring the sleeve. The complexity, tortuosity and rather dramatic changes in lumen diameter along the gastrointestinal tract present a challenge for navigation as well as placement of the anchoring structure.

The functional characteristics of the gastrointestinal tract present additional challenges when considering an appropriate structure for the sleeve anchor. The stomach is a dynamic environment in which muscular contractions aggressively break down food into chyme. During this process, the pyloric and esophageal sphincters act like valves that constrict to obstruct bolus flow and prevent the stomach contents from emptying. Chyme from the stomach is then released into the duodenum and jejunum which each exhibit rather highly compliant slippery mucosal walls that yield to the bolus flow pressure. Thus, an appropriate anchor structure for the sleeve must be capable of contending with these additional factors.

SUMMARY

The bypass device disclosed here is configured as an implantable device comprised of a sleeve and a frame structure for anchoring the sleeve in place so that the sleeve inhibits the absorption of food nutrients across the gastrointestinal tract, specifically in the duodenum and jejunum. The bypass device provides a non-invasive solution for treating type-2 diabetes and weight loss, and is configured in a way that is well-suited to the dynamic environment in which the bypass device is used.

According to one aspect, a bypass device implantable in a gastrointestinal tract of a human, which includes the small intestines, to inhibit absorption of nutrients, comprises: a support frame positionable in the gastrointestinal tract in an implanted condition of the bypass device, with the support frame possessing a central axis and extending over an axial extent between opposite axial ends of the support frame; and a liner fixed to the support frame so that in the implanted condition of the bypass device the liner is supported by the support frame and anchored in place in the gastrointestinal tract which includes small intestines, with the liner being made of a material different from the support frame and being configured to extend away from the support frame and along at least a portion of the small intestines when the support frame is positioned in the gastrointestinal tract in the implanted condition of the bypass device. The support frame comprises a plurality of frame members configured and connected to one another so that the frame members in at least a portion of the support frame define a plurality of diamond-shaped openings arranged axially and circumferentially, a plurality of the frame members each include coil springs; and at least some of the coil springs of one frame member are each connected to a respective coil spring of a different frame member by a connecting wire.

In accordance with another aspect, a bypass device implantable in a gastrointestinal tract of a human, which includes small intestines, to inhibit absorption of nutrients, comprises: a support frame positionable in the gastrointestinal tract in an implanted condition of the bypass device, with the support frame possessing a central axis and extending over an axial extent between opposite axial ends of the support frame; and a liner fixed to the support frame so that in the implanted condition of the bypass device the liner is supported by the support frame and anchored in place in the gastrointestinal tract which includes small intestines, wherein the liner is made of a material different from the support frame and being configured to extend away from the support frame and along at least a portion of the small intestines when the support frame is positioned in the gastrointestinal tract in the implanted condition of the bypass device. The support frame comprises a plurality of axially spaced apart wavy-shaped annular frame members, and each of the wavy-shaped annular frame members includes a plurality of spaced apart coil springs. In addition, a plurality of connecting wires connect axially adjacent wavy-shaped annular frame members, with each of the connecting wires connecting one of the coil springs of one of the wavy-shaped annular frame members to one of the coil springs of the axially adjacent wavy-shaped annular frame member.

Another aspect of the disclosure here involves a liner support frame configured to be positioned in a gastrointestinal tract of a human and to support a liner which inhibits nutrient absorption to anchor the liner in place in the gastrointestinal tract. The liner support frame comprises: an axially central frame portion and other frame portions positioned on opposite axial sides of the axially central frame portion, wherein the other frame portions are comprised of a plurality of axially spaced apart wavy-shaped annular frame members, with each of the wavy-shaped annular frame members including a plurality of coil springs spaced apart along the wavy-shaped annular frame member. In addition, a plurality of connecting wires connect axially adjacent wavy-shaped annular frame members, each of the connecting wires connecting one of the coil springs of one of the wavy-shaped annular frame members to one of the coil springs of the axially adjacent wavy-shaped annular frame member.

BRIEF DESCRIPTION OF DRAWINGS

FIG. 9 is a schematic illustration of a portion of the gastrointestinal tract depicting placement of the bypass device in a living body.

FIG. 10A is a perspective view of a triple wound (thrice wound) coil spring used in the support frame.

FIG. 10B is a perspective view of a double wound (twice wound) coil spring used in the support frame.

FIG. 10C is a perspective view of a single wound (once wound) coil spring used in the support frame.

DETAILED DESCRIPTION

The bypass device disclosed here includes the combination of a support frame 12 and a sleeve (liner) 14. The support frame is specifically configured for placement in a living body (human body) as will be discussed in more detail below. The sleeve (liner) is positionable along at least a portion of the gastrointestinal tract to inhibit the absorption of food nutrients across the gastrointestinal tract. The sleeve is fixed to the support frame. When the bypass device is positioned in the living body, the support frame serves as an anchor for the sleeve, helping to ensure the sleeve stays properly positioned.

Figure 1:
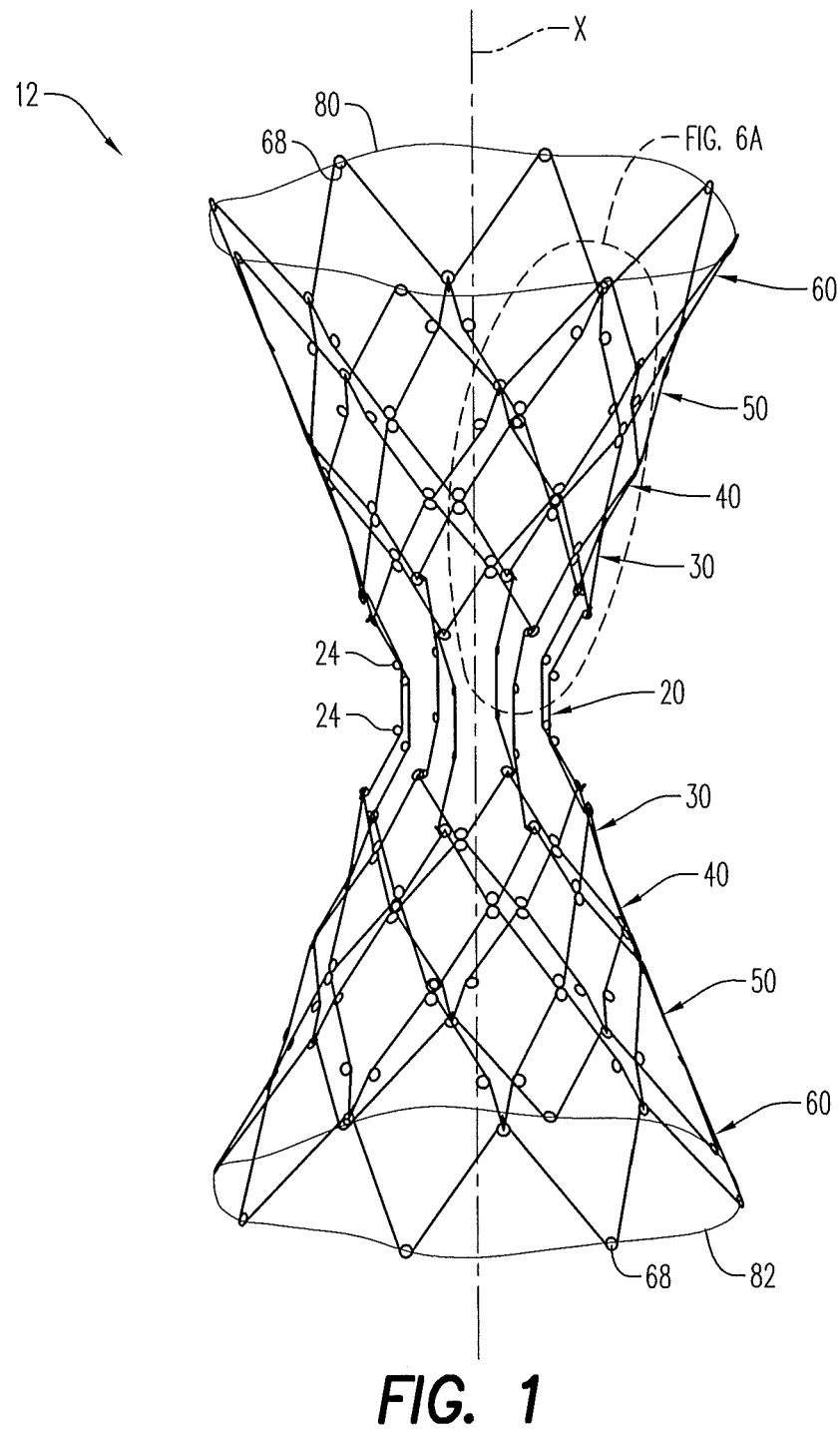
FIG. 1 is a side view of the support frame forming a part of the bypass device according to one embodiment disclosed here.

Referring initially to FIG. 1, the support frame 12 forming a part of the bypass device is a tubular member comprised of a plurality of frame members surrounding an interior of the tube-shaped support frame. The frame members are configured and connected to one another to form a plurality of openings in the support frame 12. The openings in the support frame 12 are arranged or spaced apart circumferentially and axially. With reference to FIG. 1, the upper portion of the support frame is the proximal end of the support frame (i.e., the end of the support frame facing toward the stomach when the bypass device is implanted in the living body), and the lower portion of the support frame is the distal end of the support frame (i.e., the end of the support frame facing toward the intestines when the bypass device is implanted in the living body).

Described in more detail, the support frame 12 is comprised of a plurality of first frame members 20, a plurality of second frame members 30, a plurality of third frame members 40, a plurality of fourth frame members 50 and a plurality of fifth frame members 60. In the illustrated embodiment, the support frame 12 is comprised of eight first frame members 20, a pair of second frame members 30, a pair of third frame members 40, a pair of fourth frame members 50 and a pair of fifth frame members 60. Of course, the support frame 12 is not necessarily limited in this regard.

As illustrated in FIG. 1, the first frame members 20 are positioned in the axially central portion of the support frame 12, considered with reference to the longitudinally extending central axis X. Each of the second frame members 30 axially adjoins one of the first frame members 20 and is positioned axially outwardly of the first frame members 20. Each of the third frame members 40 axially adjoins one of the second frame members 30 and is positioned axially outwardly of the respective second frame members 30, with each second frame member 30 positioned axially between the first frame members 20 and the respective third frame member 40. Each of the fourth frame members 50 axially adjoins one of the third frame members 40 and is positioned axially outwardly of the respective third frame member 40, with each third frame member 40 positioned axially between the respective second frame member 20 and the respective fourth frame member 50. Each of the fifth frame members 60 axially adjoins one of the fourth frame members 50 and is positioned axially outwardly of the respective fourth frame member 50, with each fourth frame member 50 positioned axially between the respective third frame member 30 and the respective fifth frame member 60. The fifth frame members 60 represent the axially outermost portion of the support frame 12.

Figure 2:
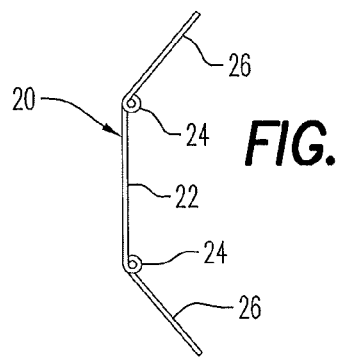
FIG. 2 is a side view of a one of the frame members forming a part of the support frame of the bypass device.

Each of the first frame members 20 is a longitudinally extending frame member extending along the longitudinal (axial) extent of the support frame 12. The frame members can be made of elastic material, for example wire, stainless steel, NiTi, Co alloys and other materials. FIG. 2 illustrates the configuration of one of the first frame members 20. It is to be understood that the other first frame members 20 are configured in the same manner. As seen in FIG. 2, each of the first frame members 20 includes a straight central part 22 extending generally parallel to the central axis X of the support frame 12, a coil spring 24 at each axial end of the straight central part 22, and a straight end part 26 extending from each of the coil springs 24 so that the straight end part 26 is angled outwardly (at an angle other than 0°) relative to the straight central part 22. As illustrated in FIG. 1, the two coil springs 24 forming a part of each of the first frame members 20 face outwardly away from the interior (the central axis) of the support frame 12 such that the axes of the coil springs 24 are at an angle with respect to the central axis of the support frame. The coil springs 24 forming a part of each of the first frame members 20 are formed as an integral, unitary part of the frame members 20. For example, if the first frame members 20 are made of wire, the wire is wound to form the coil springs 24. In this embodiment, each of the coil springs 24 forming a part of the first frame member 20 is a single wound coil spring, meaning the coil spring is formed by at least a full single winding of the material forming the frame members 20 as shown in FIG. 10C. The single wound coil spring 24 is preferably formed as 1.2 to 2.0 rotations or windings (432° to720°), more preferably between 1.5 and 1.8 rotations or windings (540° to 648°), and still more preferably 1.75 rotations or windings)(630°). The first frame members 20 are circumferentially spaced apart from one another. The first frame members 20 are preferably circumferentially spaced apart at equal angular intervals, preferably an acute angle. In the illustrated embodiment, the first frame members 20 are spaced apart at preferably 45° equal angular intervals.

Figure 3:
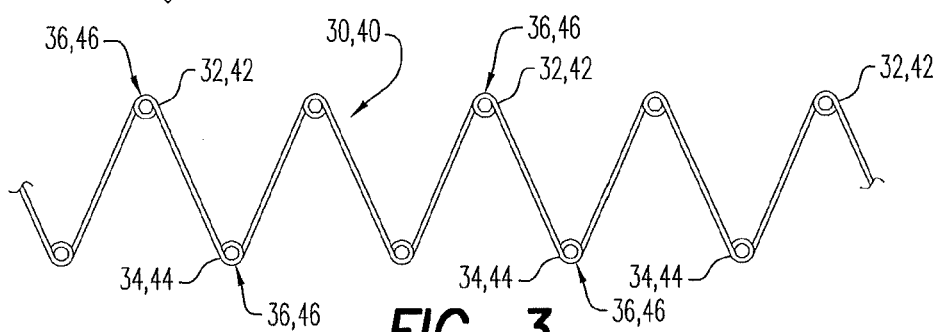
FIG. 3 is a developmental view of another one of the frame members forming a part of the support frame of the bypass device.
Figure 4:
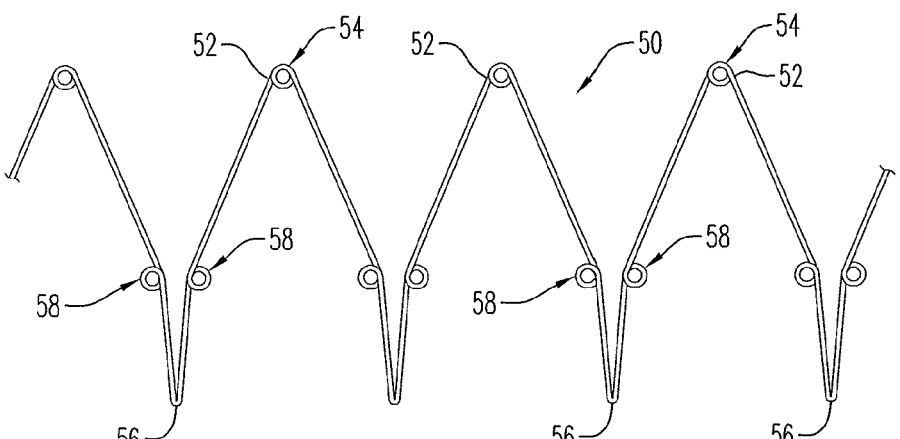
FIG. 4 is a developmental view of an additional frame member forming a part of the support frame of the bypass device.
Figure 5:
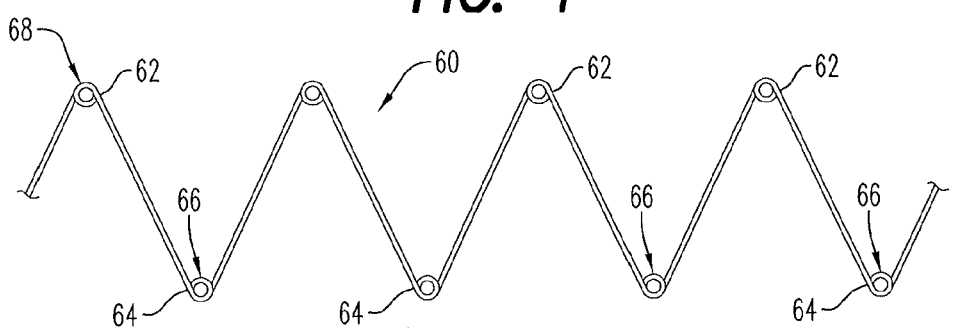
FIG. 5 is a developmental view of a further frame member forming a part of the support frame of the bypass device.

Each of the second frame members 30 and each of the third frame members 40 is in the form of a wavy-shaped annular member. FIG. 3 illustrates a developmental view of the wavy-shaped annular frame members forming the second and third frame members 30, 40. The developmental view in FIG. 3, and the developmental views in FIGS. 4 and 5, depict the configuration of the frame member if it was cut and laid flat. The wavy-shaped annular member 30, 40 shown in FIG. 3 applies to both the second and third frame members 30, 40 on the proximal side of the support frame 12, and also applies to both the second and third frame members 30, 40 on the distal side of the support frame 12.

As illustrated in FIG. 3, each of the second and third wavy-shaped annular frame members 30, 40 includes a plurality of V-shaped axial end points or peaks 32, 42. The wavy-shaped annular frame members constituting the second and third frame members 30, 40 include an alternating series of peaks 32, 42 and valleys 34, 44 as shown in FIG. 3. The peaks 32, 42 in both frame members 30, 40 are at the axial end of the frame member farther from the frame members 20, while the valleys 34, 44, 42 in both frame members 30, 40 are at the axial end of the frame member closer to the frame members 20.

The wavy-shaped annular frame members also include a coil spring 36, 46 at each of the peaks 32, 42 and a coil spring 36, 46 at each of the valleys 34, 44. The coil springs 32, 42, 36, 46 forming a part of the respective second and third frame members 30, 40 are formed as an integral, unitary part of the respective frame members. In this disclosed embodiment of the support frame, each of the coil springs 32, 42, and each of the coil springs 36, 46 is a double wound coil spring, meaning each coil spring 36, 46 is formed by at least a full double winding of the material forming the frame members inside of the peaks or valleys. That is, the coil springs are located on the interior of the two legs forming the peak/valley. The coil springs inside the peaks or valleys flexibly ensure that overall structure is maintained. And the distance between the wavy-shaped annular frame members is fixed or flexibly changeable, preferably flexibly changeable.

The coil springs 32 of each respective second frame member 30 preferably lie in a generally common plane, and the coil springs 36 of each respective second frame member 30 preferably also lie in a common plane, when the wavy-shaped annular frame members are placed on a planar surface. Similarly, the coil springs 42 of each respective third frame member 40 preferably lie in a common plane, and the coil springs 46 of each respective third frame member 40 preferably also lie in a common plane, when the wavy-shaped annular frame members are placed on a planar surface. The generally common plane includes a fair (flat) plane, a flat plane, a curved plane or a rounded plane.

Each of the fourth frame members 50 is a wavy-shaped annular frame member. The fourth wavy-shaped annular frame members 50 are configured slightly differently compared to the second and third wavy-shaped annular frame members 30, 40. One of the fourth frame members 50 is shown in FIG. 4 which illustrates the fourth frame member 50 in the upper half of the support frame 12 (the upper half shown in FIG. 1). The fourth frame member 50 in the lower half of the support frame 12 (the lower half shown in FIG. 1) is oriented the opposite of the orientation of the fourth frame member 50 in the upper half of the support frame. As illustrated in FIG. 4, each of the fourth wavy-shaped annular frame members 50 includes a plurality of V-shaped axial end points 52 at each of which is located a coil spring 54. The opposite axial end of each fourth wavy-shaped annular frame member 50 is configured to include a plurality of protrusions 56 which are somewhat narrowed as illustrated in FIG. 4. The protrusions 56 in each frame member 50 are at the axial end of the frame member 50 farther from the axially central frame members 20, while the V-shaped axial end points 52 and the coil springs 54 in each frame member 50 are at the axial end of the frame member 50 closer to the axially central frame members 20. The coil springs 54 are each located at an interior of the V-shaped axial end points 52 (i.e., between the two legs forming the V-shaped axial end points 52).

As explained above, the fourth wavy-shaped annular frame members 50 positioned in the upper half of the support frame 12 in FIG. 1 is oriented opposite the orientation of the fourth wavy-shaped annular frame members 50 positioned in the lower half of the support frame 12 in FIG. 1. Thus, with the support frame 12 positioned as shown in FIG. 1, the V-shaped axial end points 52 in the fourth wavy-shaped annular frame members 50 located in the upper half of the support frame 12 in FIG. 1 represent valleys, whereas the V-shaped axial end points 52 in the fourth wavy-shaped annular frame members 50 located in the lower half of the support frame 12 in FIG. 1 represent peaks.

At the base of each protrusion 56 is located a pair of spaced apart coil springs 58. All of the coil springs 58 in each respective wavy-shaped annular fourth frame member 50 are preferably positioned in a common plane, when the wavy-shaped annular frame members are placed on a planar surface. Similarly, all of the coil springs 54 in each respective wavy-shaped annular fourth frame member 50 are preferably positioned in a common plane, when the wavy-shaped annular frame members are placed on a planar surface. Each of the coil springs 58 is preferably a thrice wound coil spring, meaning each coil spring 58 is formed by at least a full triple winding of the material forming the frame members 50 (see FIG. 10A). That is, each coil spring 58 is formed by at least a 1080° winding of the material forming the frame members. The thrice wound coil springs 58 (and the coil springs 68 discussed below) are preferably formed as 3.2 to 4.0 rotations or windings (1152° to 1440°), more preferably between 3.5 and 3.8 rotations or windings (1260° to 1368), and still more preferably 3.75 rotations or windings (1350°). Each of the coil springs 54 is preferably a twice wound coil spring, meaning each coil spring 54 is formed by at least a full double winding of the material forming the frame members 50 (see FIG. 10B). That is, each coil spring 54 is formed by at least a 720° winding of the material forming the frame members. The coil springs 54, 58 forming a part of the respective frame members 50 are formed as an integral, unitary part of the respective frame members 50. The twice wound coil springs 54 (and the coil springs 66 discussed below, as well as the coil springs 36, 46) are each preferably formed as 2.2 to 3.0 rotations or windings (792° to 1080°), more preferably between 2.5 and 2.8 rotations or windings (900° to 1008), and still more preferably 2.75 rotations or windings (990°).

The fifth frame member 60 is also a wavy-shaped annular frame member as illustrated in FIGS. 1 and 5. FIG. 5 shows that the wavy-shaped annular frame member 60 includes a plurality of V-shaped axial end points or alternating peaks 62 and valleys 64. The peaks 62 in each frame member 60 are at the axial end of the frame member 60 farther from the axially central frame members 20, while the valleys 64 in each frame member 60 are at the axial end of the frame member 60 closer to the axially central frame members 20.

The wavy-shaped annular frame member constituting the fifth frame member 60 includes a coil spring 66 at each valley 64 and a coil spring 68 at each peak 62. Each of the coil springs 66 at each of the valleys 64 is preferably a double wound coil spring, meaning each coil spring 66 is formed by at least a full double winding of the material forming the frame member 60 (see FIG. 10B). That is, each coil spring 66 is formed by at least a 720° winding of the material forming the frame members similar to the coil springs 54. Each of the coil springs 68 at each peak 62 of the wavy-shaped frame member 60 is preferably a thrice wound coil spring, meaning each coil spring 66 is formed by at least a full triple winding of the material forming the frame member 60 (see FIG. 10A). That is, each coil spring 68 is formed by at least a 1080° winding of the material forming the frame members similar to the coil springs 58. The coil springs 66, 68 forming a part of the respective frame members 60 are formed as an integral, unitary part of the respective frame members 60. The coil springs 66 of each respective fifth frame member 60 preferably lie in a common plane, and the coil springs 68 of each respective fifth frame member 60 preferably also lie in a common plane, when the wavy-shaped annular frame members are placed on a planar surface. The coil springs 66 are each positioned on an interior of the peak/valley as illustrated.

Referring once again to FIG. 1, each end of each of the first frame members 20 is connected to the coil spring 36 at the valley of the axially adjacent second frame member 30 at respective connection points. These connection points connecting the first frame members 20 to the respective coil spring 36 of the axially adjacent second frame member 30, are illustrated in more detail in FIGS. 6A and 6D, and involve the end portion 27 of the first frame members 20 passing through the respective coil 36, several times in the illustrated embodiment, and then twisting the end portion 27 of the first frame portion to secure the end portion of the first frame member 20 to the respective coil spring 36.

Figure 6A:
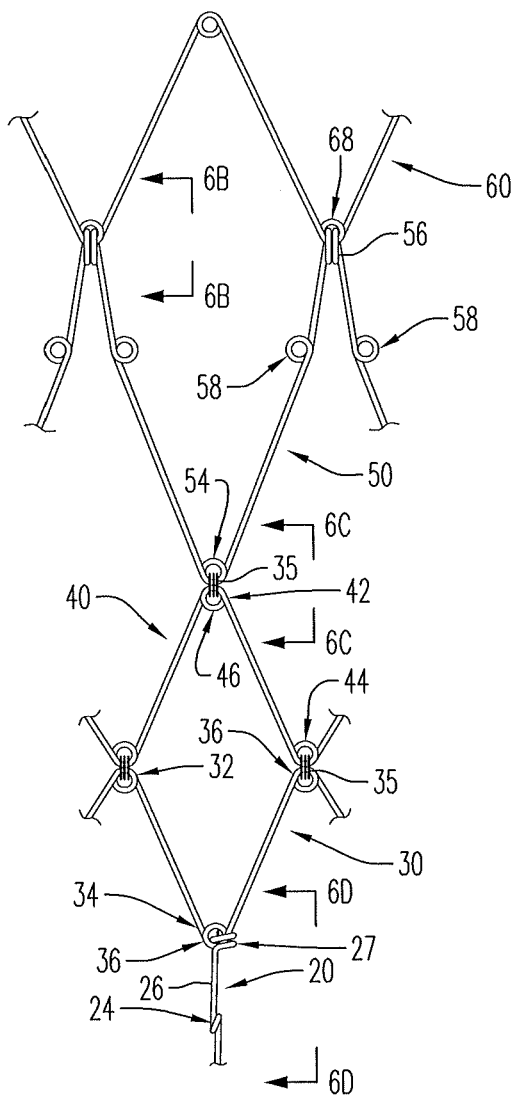
FIG. 6A is an enlarged side view of the portion of the support frame shown in FIG. 1 outlined in dotted line and identified as FIG. 6A, illustrating details of the connection points connecting frame members of the support frame.
Figure 6B:
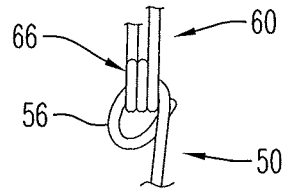
FIG. 6B is an enlarged view of the portion of the support frame shown in FIG. 6A as seen from the direction of the arrows 6B.
Figure 6C:
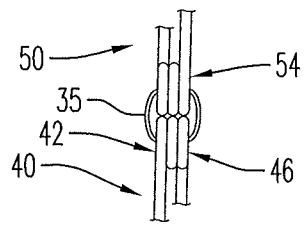
FIG. 6C is an enlarged view of the portion of the support frame shown in FIG. 6A as seen from the direction of the arrows 6C.
Figure 6D:
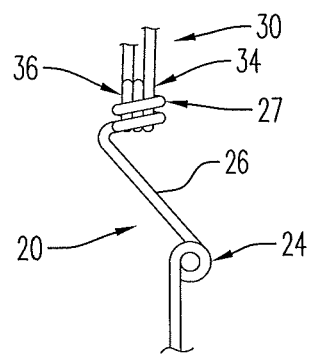
FIG. 6D is an enlarged view of the portion of the support frame shown in FIG. 6A as seen from the direction of the arrows 6D.

As seen in FIG. 1, the wavy-shaped annular second frame members 30 are connected to the axially adjacent wavy-shaped annular third frame members 40 at respective connection points. These connection points, connecting axially adjacent wavy-shaped annular second and third frame members 30, 40, are illustrated in more detail in FIGS. 6A and 6C, and involve a suture or connection wire 35. The suture or connection wire 35 connects axially adjacent coil springs 36, 46 of axially adjacent frame members 30, 40. For example, the suture or connection wire 35 connects the coil spring 36 at a peak 32 of the wavy-shaped annular second frame member 30 to a respective coil spring 46 at the valley of the wavy-shaped annular fourth frame member 40. The suture or connection wire 35 is preferably separate and apart from the support frames. The suture or connecting wire 35 passes through each of the respective coil springs and is then twisted or otherwise tied off to secure together the adjoining coil springs. As illustrated in FIGS. 6A and 6C, some of the axially adjacent coil springs 36, 44 (i.e., the coil springs 36, 44 located closer to the axial center of the support frame) are wound in different directions. Specifically, the coil spring 36 of the second frame member 30 is wound in the counterclockwise direction and the coil spring 44 of the third frame member 40 is wound in the clockwise direction. As further illustrated in FIGS. 6A and 6C, some of the axially adjacent coil springs 46, 54 (i.e., the coil springs 46, 54 located farther away from the axial center of the support frame) are wound in the same direction. Specifically, the coil spring 46 of the third frame member 40 and the coil spring 54 of the fourth frame member 50 are both wound in the counterclockwise direction.

The wavy-shaped annular fourth frame member 50 is connected to the wavy-shaped annular fifth frame member 60 at respective connection points. The connection points connecting the fourth frame member 50 and the fifth frame member 60 are best seen in FIGS. 6A and 6B. The connection points between the fourth frame member 50 and the fifth frame member 60 involves each of the protrusions 56 on the fourth frame member 50 being fitted into and bent around one of the coil springs 66 forming a part of the fifth frame member 60. This is illustrated in FIG. 6B which depicts the protrusion 56 passing though the coil spring 66 of the adjacent frame member 60. The protrusions 56 thus form hooks that engage the respective coil springs 66.

Figure 7:
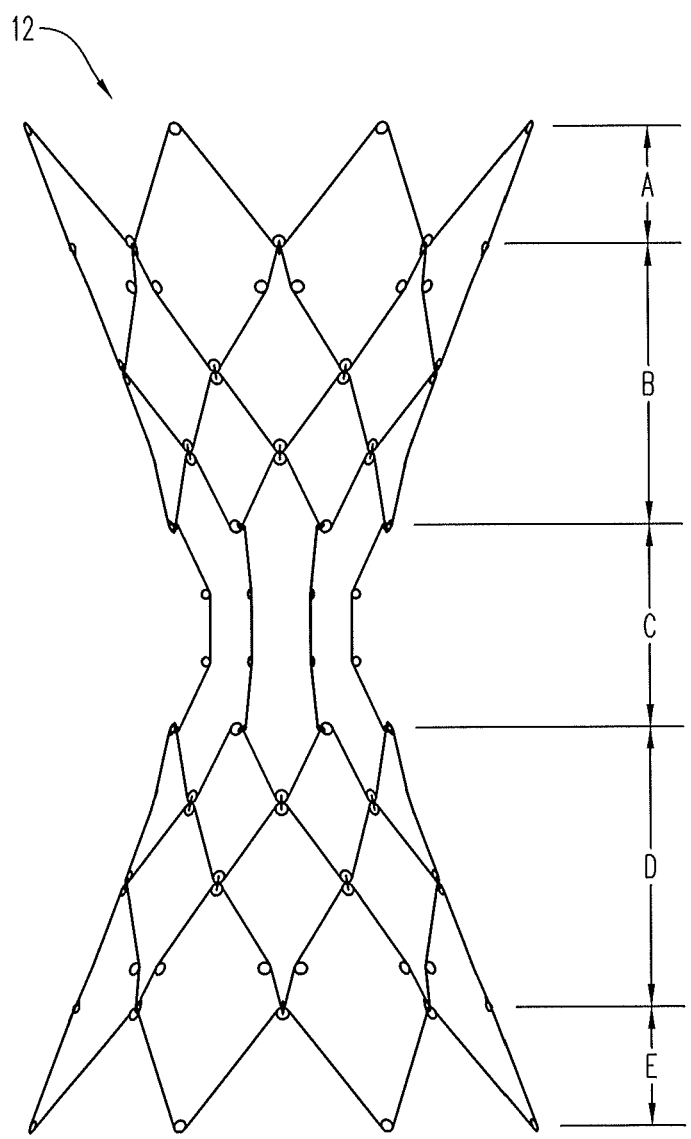
FIG. 7 is a side view of the support frame shown I FIG. 1, identifying different sections of varying flexibility.

By virtue of the configuration of the frame members forming the support frame, and the way in which the adjoining frame members 20, 30, 40, 50, 60 are connected to one another as described above, the support frame 12 exhibits different flexibility characteristics along its length or axial extent. Referring to FIG. 7, which is an illustration of the support frame shown in FIG. 1 but without the reference numerals, the support frame 12 includes five sections exhibiting different flexibility characteristics. The term "flexibility" as used here refers to the radial force required to inwardly deform the support frame. Thus, a section of the support frame which is more flexible requires a lesser radial force to inwardly deform the support frame, whereas a less flexible section requires a greater force to inwardly deflect the support frame the same amount.

Referring to FIG. 7 the flexibility of the frame section B is less than the flexibility of the frame section D, and the flexibility of the frame section D is less than the flexibility of the support frame section C. This relationship of the flexibility of the frame sections, B, D, C is expressed as follows:

$$B<D<C \tag{i}$$

Referring still to FIG. 7, the flexibility of the support frame section B is less than the flexibility of the frame section A, and the flexibility of the frame section D is less than the flexibility of the frame section E. These flexibility relationships can be expressed in the following way:

$$B<A \text{ and } D<E \tag{ii}$$

The flexibility of the frame sections can be varied by, for example, using a different diameter wire, varying the elastic force of the wire, and using a different number and/or size of the diamond-shaped openings/spaces between axially adjacent frame sections.

It is possible for all of the frame sections to exhibit different flexibility so long as the flexibility relationships above (i) and (ii) are satisfied. Similarly, it is possible for some of the frame sections to exhibit the same flexibility so long as the flexibility relationships above (i) and (ii) are satisfied. In the illustration in FIG. 7, frame section A is located at the proximal side of the support frame (proximal-most portion of the support frame), while the frame section E is located at the distal side of the support frame (distal-most portion of the support frame). As will be discussed in more detail below, when the support frame is mounted in the gastrointestinal tract, the sleeve (liner) supported by the support frame 12 will extend distally beyond the distal end of the support frame 12 and will appropriately positioned in the cited portion of the gastrointestinal tract.

FIG. 7 also illustrates that the shape of the openings in the support frame 12 in frame section C differs from the shape of the openings in the other frame sections B, A, D, E. In particular, the openings in the frame sections A, B, D, E are diamond-shaped openings, whereas the openings in the frame section C are other than diamond-shaped openings. Generally speaking, the openings in the frame section C, representing the axially central portion of the support frame, are a combination of square(s) in the middle portion and V-shape(s) at the ends, for example a hexagonal shape.

FIG. 7 also illustrates that the size of the diamond-shaped openings in the frame sections A, B, D, E varies along the axial extent of the support frame. As illustrated, the diamond-shaped openings that are closer to the axial center of the support frame (i.e., closer to the axially center frame section C) are smaller in size than the diamond-shaped openings positioned farther from the axial center of the support frame. In a similar manner, FIG. 7 illustrates that the perpendicular distance between the central axis of the support frame and each of the coil springs is greater for the coil springs located axially further from the central portion of the support frame than for the coil springs located axially closer to the central portion of the support frame.

As will be discussed in more detail below, the bypass device is preferably positioned in the gastrointestinal tract so that the support frame 12 straddles the pyloric ring. More specifically, the support frame is positioned so that the pyloric ring is located at the axially central frame section C of the support frame, the frame sections A, B on the proximal end of the support frame 12 are positioned on the pylorus side of the pyloric ring, and the frame sections D, E on the distal end of the support frame 12 are positioned on the duodenal bulb side of the pyloric ring. The axially central frame section C formed in the illustrated manner to produce the above-mentioned flexibility characteristics is desirable because it does not interfere with the contraction of the pyloric ring and does not interfere with the passage of food through the pyloric ring. Thus, the axially central frame section C is positioned on the pyloric ring and so the diameter of section C is smaller than other sections, and the section C is relatively flexible because the axially central frame section C is closed by the movement of pyloric ring. Thus, the axially central frame section C possesses the smallest outer diameter (and inner diameter) relative to all other frame sections of the support frame 12, and possesses a generally concave outer shape, in an axial direction, as seen from the side (FIG. 1), with a straight central portion.

The frame section B, which is the least flexible frame section as between the five frame sections A-E, is characterized by a diamond structure, meaning that the interconnected frame members in the frame section B form a plurality of circumferentially and axially spaced apart diamond-shaped openings. This particular structure and the resulting stiffness of the frame section B helps ensure that the support frame does not pass through the pyloric ring. The configuration of frame section B and its resulting stiffness characteristics makes this frame section rather difficult to crush thus providing good resistance to peristalsis. It is also difficult to fold this section B inwardly such that it would be pulled to the pyloric ring side of the small-diameter state. The frame section B is thus configured to be relatively hard (least flexible) because the frame section B is positioned in the stomach proximal to the pyloric ring and is thus configured so the frame section B is prevented from moving into the pyloric ring. In addition to being the least flexible, the frame section B possesses a larger outer (and inner) diameter than the axially central frame section C to thus apply a radial force that helps prevent the frame section B from moving into the pyloric ring.

The frame section D also includes a diamond structure like section B, meaning that the interconnected frame members in the frame section D form a plurality of circumferentially and axially spaced apart diamond-shaped openings. But section D is less stiff and more flexible than section B. This frame section D is thus configured to maintain a size that does not allow it to pass through the pylorus, thus resisting reverse peristalsis. On the other hand, the stiffness of this frame section D is not so high as to cause damage to the intestinal tissue. This is a point that is of concern because the intestinal tissue is relatively thin.

The frame section A at the proximal-most end portion of the support frame 12 is defined by the wavy-shaped frame member 60 and forms a flower structure (i.e., the frame section A resembles a flower with petals) at the proximal end of the support frame 12. This flower structure is configured in the manner shown in FIG. 7, involving a plurality of axially directed and radially outwardly triangular shaped elements that are circumferentially arranged. As discussed above, the connection between the wavy-shaped annular fifth frame member 60 and the axially adjacent wavy-shaped annular frame member 50 is achieved by hooks. That is, the protrusions on the wavy-shaped frame member 50 fit into or hook into the coil springs on the wavy-shaped annular frame member 60. This results in a stiffness in the frame section A that is soft-hard, meaning the frame section A can be relatively softer (in which case it is not likely to damage the stomach) or relatively harder (in which case it is likely to help prevent movement into the pyloric ring), so long as the relationships i and ii above are met. This structure at the proximal end of the support frame 12 provides alignment along the stomach wall, thereby reducing the pressure burden on the stomach wall during indwelling, to facilitate the passage of food. The hooks also allow the open proximal end of the support frame 12 to be closed when a string passing through the coils at the proximal-most end of the wavy-shaped annular frame member 60 is pulled as will be described below in more detail.

The frame section E at the distal-most end portion of the support frame 12 is defined by the wavy-shaped frame member 60 in the frame section E and forms a flower structure at the proximal end of the support frame 12. The connection between the wavy-shaped annular fifth frame member 60 and the axially adjacent wavy-shaped annular frame member 50 in the frame section D results in a stiffness in the frame section E that is soft-mild. This stiffness referred to as soft-mild means that the stiffness is less than hard. That is, the frame section E is soft and therefore does not damage the intestine yet helps pass foods. This stiffness is selected so as not to damage the intestinal tissue because the intestinal tissue is rather thin. The structure at the distal end of the support frame 12 provides alignment along the intestinal wall to reduce the pressure burden on the intestinal wall during indwelling, thus facilitating the passage of food. The hooks also allow the open distal end of the support frame 12 to be closed when a string passing through the coils at the distal-most end of the wavy-shaped annular frame member 60 is pulled as will be described below in more detail.

Thus, referring to FIG. 7, beginning at the proximal-most end of the support frame 12, the section A is relatively soft, section B is relatively hard, section C is relatively soft, section D is relatively hard and section E is relatively soft. The term "hard" as used here is another way of referring to the relative flexibility of the different sections. Thus, sections A, C and E are relatively more flexible (relatively less stiff) while sections B and D are relatively less flexible (relatively more stiff). Thus, applying the same radially inward force to each of the sections A-E, sections A, C and E will deform more than sections B and D. From the standpoint of the shape of the different frame sections A-E, the frame section A is the shape of a flower, the frame section B is the shape of diamonds, the frame section C is the shape of concave straight sections, the frame section D is the shape of diamonds and the frame section E is the shape of a flower.

Figure 8:
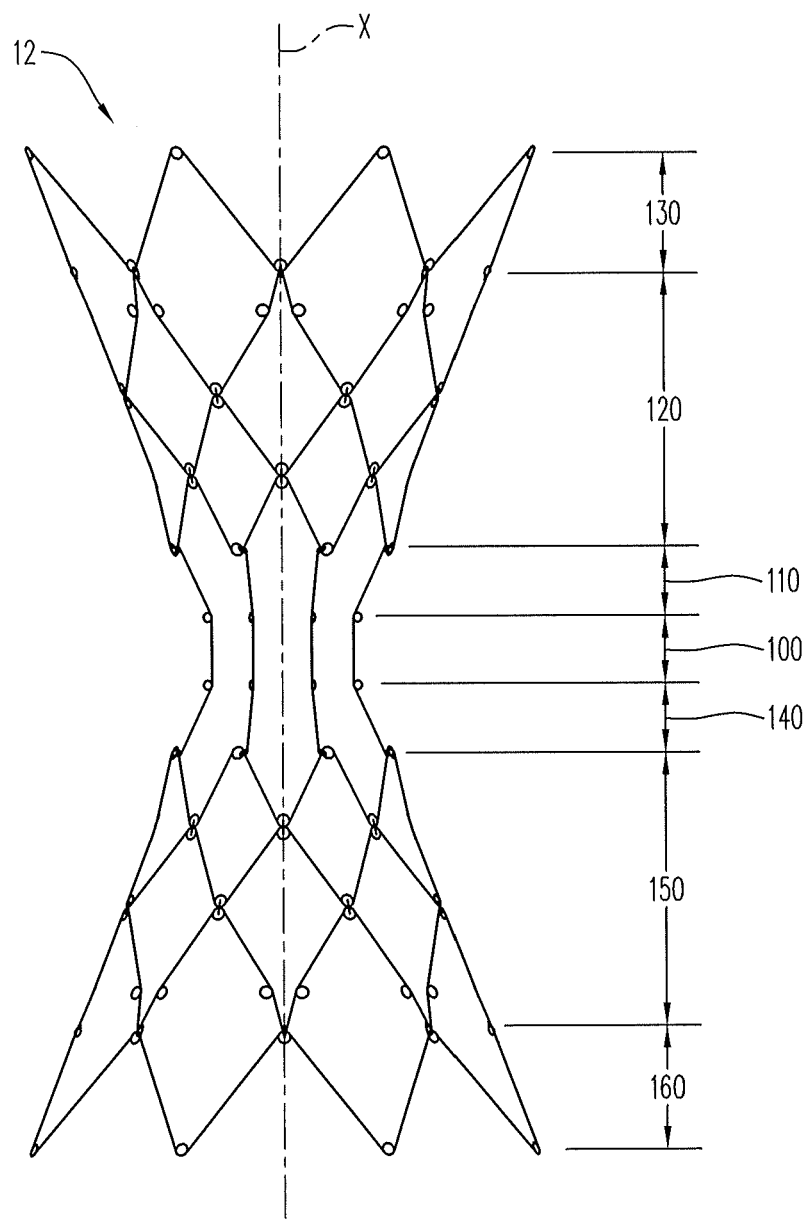
FIG. 8 is a side view of the support frame shown I FIG. 1, identifying different taper portions of the support frame.

The support frame 12 is also configured to include a plurality of axially arranged frame portions having different taper characteristics. Referring to FIG. 8, which is another illustration of the support frame 12 shown in FIG. 1 but without the reference numerals, the support frame 12 includes an axially central frame portion 100, a plurality of other frame portions 110, 120, 130 on the proximal side of the axially central frame portion 100, and a plurality of other frame portions 140, 150, 160 on the distal side of the axially central frame portion 100. The frame portions on the proximal side of the axially central frame portion 100 include a first taper portion 110, a second taper portion 120, and a third taper portion 130. Each of these taper portions 110, 120, 130 taper outwardly relative to the central axis X of the support frame. Each of the frame sections 110, 120, 130 is thus configured so that its outer surface diverges in a direction away from the axially central frame portion 100. The taper angle of each of the three taper sections 110, 120, 130 is different from one another. To fit the pylorus, the taper angle of the taper section 110 is greater than the taper angel of each of the taper sections 120, 130.

The frame sections in the distal portion of the support frame include a first taper section 140, a second taper section 150 and a third taper section 160. The taper angles formed by each of the sections 140, 150, 160 are different from one another. Each of the frame sections 140, 150, 160 is thus configured so that its outer surface diverges in a direction away from the axially central frame portion 100. In addition, the taper angles of each of the sections 140, 150, 160 on the distal portion of the frame support can be the same as or different from the taper angles of each of the sections 110, 120, 130 on the proximal portion of the frame support. The cross section of the support frame in each of the taper sections 110, 120, 130, 140, 150, 160 possesses a multi-angle or multi-side shape, for example an octa-angle or eight-sided shape shape.

As illustrated in FIG. 1, both the proximal end of the support frame and the distal end of the support frame are open. The support frame 12 includes a pullwire 80 at the proximal end of the support frame and a separate pullwire 82 at the distal end of the support frame. Each of the pullwires 80, 82 is preferably an endless or continuous pullwire. The pullwire 80 at the proximal end of the support frame passes through the coil springs 68 at the proximal-most end of the support frame 12. Similarly, the pullwire 82 passes through the coil springs 68 of the wavy-shaped annular frame member 60 at the distal-most end of the support frame 12. By pulling on the pullwire 80, it is possible to close the open proximal end of the support frame by drawing together the proximal-most end portions (i.e., the flowers) of the support frame. Similarly, pulling on the pullwire 82 closes the open distal end of the support frame by pulling together the proximal-most end portions (i.e., the flowers) of the support frame 12.

FIG. 9 is a schematic illustration of a portion of the gastrointestinal tract of a human (living body) to provide an illustration of placement of the bypass device 10 disclosed here. As illustrated in FIG. 9, the pyloric ring or pyloric sphincter P is positioned between the stomach S and the duodenum bulb D. As is known, the duodenum bulb leads to the duodenum which in turn leads to the jejunum.

The bypass device 10 disclosed here is configured to cross the pyloric ring P. That is, the pyloric ring P is positioned in the axially central portion of the support frame (i.e., the frame section C of the support frame 12 illustrated in FIG. 7). The portion of the support frame 12 on the proximal side of the axially central section generally extends into the stomach S while the portion of the support frame 12 on the distal side of the axially central frame section is positioned in the duodenal bulb D.

As discussed above, the bypass device 10 includes the support frame in combination with a sleeve or liner. As generally shown in FIG. 9, the sleeve 14 is fixed to the support frame 12 in any suitable manner known in the art so that the sleeve 14 is held by the support frame 12. The sleeve 14 extends distally beyond the distal-most end of the support frame into the small intestine. The sleeve or liner 14 can be made of any suitable material known in the art for these types of gastrointestinal devices.

The general process or operation for inserting the bypass device 10 into the intended place in a human body such as shown in FIG. 9 is as follows. A delivery device is used to deliver the bypass device. The delivery device includes an inner catheter, an outer catheter or both an inner catheter and an outer catheter. The bypass device 10 (the support frame 12 and the sleeve or liner 14) is then placed on the inner catheter, in the outer catheter, or between inner and outer catheter. The distal end of the delivery device and the bypass device are then delivered into the small intestine via the mouth and the stomach. Next, the delivery device is removed from the small intestine. The support frame 12 is located in the duodenum bulb and the stomach, by first inflating the distal end of the support frame in the duodenum bulb and second inflating the proximal end of the support frame in the stomach. The axial central frame section C is located at the pyloric ring P. With the support frame 12 properly positioned, the sleeve or liner 14 is then extended from the distal end of the support frame.

The support frame disclosed here is specifically configured for use as a bypass device in the manner described above. The support frame is well suited to reliably anchoring the sleeve or liner in place without damaging intestinal tissue in the body. The support frame is able to contend with the motion of the stomach, the operation of the pyloric ring or pyloric sphincter, and intestinal wall compliance.

The detailed description above describes features and aspects of a bypass device, a frame structure for a bypass device and a method. The invention is not limited, however, to the precise embodiment and variations described. Various changes, modifications and equivalents could be effected by one skilled in the art without departing from the spirit and scope of the invention as defined in the appended claims. It is expressly intended that all such changes, modifications and equivalents which fall within the scope of the claims are embraced by the claims.

What is claimed is:

1. A bypass device implantable in a gastrointestinal tract of a human, which includes small intestines, to inhibit absorption of nutrients, the bypass device comprising:
a support frame positionable in the gastrointestinal tract in an implanted condition of the bypass device, the support frame possessing a central axis and extending over an axial extent between opposite axial ends of the support frame;
a liner fixed to the support frame so that in the implanted condition of the bypass device the liner is supported by the support frame and anchored in place in the gastrointestinal tract which includes small intestines, the liner being made of a material different from the support frame and being configured to extend away from the support frame and along at least a portion of the small intestines when the support frame is positioned in the gastrointestinal tract in the implanted condition of the bypass device;
the support frame comprising a plurality of frame members configured and connected to one another so that the frame members in at least a portion of the support frame define a plurality of diamond-shaped openings arranged axially and circumferentially;
a plurality of the frame members each including coil springs;
first coil springs of one frame member each being connected to a respective coil spring of a different frame member by a connecting wire;
a direction of winding of the first coil springs of one frame member and a direction of winding of the respective coil spring of the different frame member connected by one of the connecting wires being different;
second coil springs of the one frame member each being connected to a respective coil spring of a third frame member by a connecting wire, the second coil springs of the one frame member and the respective coil spring of the third frame member connected by one of the connecting wires being wound in a same direction; and
the support frame including a central portion at an axial central portion of the support frame and end portions at opposite axial ends of the support frame, the one frame member possessing a central frame side located toward the central portion of the support frame and also possessing an end frame side located toward the end portion of the support frame, the first coil springs being at the central frame side and the second coil springs being at the end frame side.

2. The bypass device according to claim 1, wherein the one frame member possesses a shape different from the shape of the different frame member.

3. The bypass device according to claim 1, wherein the one frame member and the third frame member possess the same shape, and the one frame member possesses a shape different from the shape of the different frame member.

4. The bypass device according to claim 3, wherein the different frame member includes a protrusion protruding axially from a base, with a pair of spaced apart coil springs.

5. The bypass device according to claim 4, wherein the pair of spaced apart coil springs are positioned between opposite axial ends of the different frame member.

6. The bypass device according to claim 1, wherein the support frame possesses a tapered portion at which an outer dimension of the support frame narrows so that respective axes of the coil springs are at an angle with respect to a central axis of the support frame.

7. The bypass device according to claim 6, wherein the support frame includes an axially central portion, and a perpendicular distance between the central axis of the support frame and each of the coil springs is greater for the coil springs located axially further from the central portion of the support frame than for the coil springs located axially closer to the central portion of the support frame.

* * * * *